United States Patent [19]

Brandt

[11] Patent Number: 5,672,809

[45] Date of Patent: Sep. 30, 1997

[54] METHOD AND APPARATUS FOR DETERMINING THE PERFORMANCE OF SPORTS BATS AND SIMILAR EQUIPMENT

[76] Inventor: Richard A. Brandt, 221 W. 13th St., New York, N.Y. 10011

[21] Appl. No.: 608,672

[22] Filed: Feb. 29, 1996

[51] Int. Cl.[6] .................................................. G01N 3/30
[52] U.S. Cl. .......................... 73/12.01; 73/65.03; 473/451; 124/65
[58] Field of Search ........................... 73/12.02, 12.09, 73/65.03, 11.01; 473/422, 451, 468, 563; 273/107; 124/16, 34, 55, 65

[56] References Cited

U.S. PATENT DOCUMENTS

| | | | |
|---|---|---|---|
| 2,749,902 | 6/1956 | Foster | 124/65 |
| 3,093,995 | 6/1963 | Gordon | 73/12.02 |
| 3,364,751 | 1/1968 | Cornell et al. | 73/432 |
| 3,509,736 | 5/1970 | Saari | 73/13 |
| 3,792,861 | 2/1974 | Coleman | 124/16 X |
| 3,905,223 | 9/1975 | Ludloff | 73/65 |
| 4,006,626 | 2/1977 | Rizicka et al. | 73/12.02 |
| 4,212,193 | 7/1980 | Turley | 73/65 |
| 4,291,574 | 9/1981 | Frolow | 73/65.03 |
| 4,959,807 | 9/1990 | Thompson et al. | 364/565 |
| 5,118,102 | 6/1992 | Bahill | 273/25 |
| 5,170,663 | 12/1992 | Kovacevic | 73/379 |
| 5,170,664 | 12/1992 | Hirsh et al. | 73/493 |
| 5,267,549 | 12/1993 | Webber | 124/65 |
| 5,269,177 | 12/1993 | Miggins et al. | 73/65.03 |
| 5,377,656 | 1/1995 | Lewinski et al. | 124/65 |
| 5,538,453 | 7/1996 | Johnson | 124/65 X |
| 5,590,875 | 1/1997 | Young | 473/451 X |
| 5,590,876 | 1/1997 | Sejnowski | 473/451 X |
| 5,597,160 | 1/1997 | Mims | 124/16 |

*Primary Examiner*—Elizabeth L. Dougherty
*Attorney, Agent, or Firm*—Irwin Ostroff; Erwin W. Pfeifle

[57] ABSTRACT

A system for determining the performance of a first piece of sport equipment mounts the first piece of sports equipment such as a bat, golf club, tennis racket, or hockey stick having known characteristics of a Moment of Inertia, a weight, and a location of a Center of Mass for impact by a second piece of sports equipment which has a known Coefficient of Restitution in a mounting device. The mounting device is arranged to freely move the first piece of sports equipment from a predetermined starting position when the first piece of sports equipment is impacted substantially at a center of a predetermined impact area thereof by the second piece of sports equipment moving at a velocity "v". A measuring device measures (a) the velocity "v" of the second piece of sports equipment propelled at the center of a predetermined impact area, and (b) the rebound velocity "V" of the first piece of sports equipment as the first piece of sports equipment moves after it has been impacted by the second piece of sports equipment. The known characteristics of the first and second pieces of sports equipment and the rebound velocity of the first piece of sports equipment and the velocity of the second piece of sports equipment are used to determine a Coefficient of Restitution (COR) between the first and second pieces of sports equipment, and a performance factor for the first piece of sports equipment.

28 Claims, 2 Drawing Sheets

METHOD AND APPARATUS FOR DETERMINING THE PERFORMANCE OF SPORTS BATS AND SIMILAR EQUIPMENT

FIELD OF THE INVENTION

The present invention relates to a method and apparatus for defining and determining the performance of a softball or baseball bat or similar sports equipment such as golf clubs, hockey sticks, and tennis rackets that strike another piece of sports equipment such as a ball or hockey puck during playing of a game.

BACKGROUND OF THE INVENTION

In order to more closely control conditions of play in sports games, it is desirable for manufacturers of sports equipment and the organizations sponsoring tournaments or league play to standardize the sports equipment used in order to ensure fair play and safety. Techniques are available to test or measure different parameters of various sports equipment such as baseball bats, golf balls, golf clubs, etc.

U.S. Pat. No. 3,509,736 (Saari), issued on May 5, 1970, discloses apparatus for testing impact reactions of resilient bodies such as golf balls to impacts applied thereto at a predetermined speed by a rotating striker member. The apparatus comprises a retractable striker member, a device for moving golf balls to a tee, and a light beam and a light screen that are spaced apart at a predetermined distance equal to a circumference of the striker. A measurement of the time required for the ball to move between the light beam and the light screen, and for the striker to make one revolution permits a Coefficient of Restitution of the ball to be computed by a computer for any velocity of impact and then displayed.

U.S. Pat. No. 4,212,193 (Turley), issued on Jul. 15, 1980, discloses apparatus and method for measuring a moment of inertia of golf clubs, and like objects, about any spin axis remote from the center of gravity of the object. The apparatus comprises a holder and a single resilient member. The holder holds the object to be measured with the spin axis lying vertically. The single resilient member is located at the spin axis and supports the holder and the object in a cantilever fashion. The resilient member also allows only oscillatory rotational movement of both the holder and the object in a horizontal plane about the spin axis, and provides a restoring force proportional to any rotational displacement of the holder and the object away from their neutral position for which the restoring force is zero. In this manner, the holder and the object can be displaced and then released to enable the oscillatory rotational movement to occur and a single measurement of the oscillation to be made from which the moment of inertia about the spin axis of the object can be calculated without other measurements.

U.S. Pat. No. 5,118,102 (Bahill et al.), issued on Jun. 2, 1992, discloses an instrument for measuring a player's bat speed. The instrument comprises first, second, third, fourth, fifth, and sixth means. The first means is used to obtain data on bat speed for each bat of a plurality of diversely weighted bats that a player swings, where each bat is swung a predetermined number of times. To obtain such data the first means can comprise first and second spaced-apart light detecting means located so that the center of gravity of the bat passes therethrough during a swing of the bat. The second means plots a point of each corresponding bat weight versus the bat speed data that was determined by the first means. The third means functions to fit a best fit curve to a plot of the points of the bat weight versus the bat speed data obtained by the second means. The fourth means uses the best fit curve from the third means to obtain a mathematical equation for the speed of the bat before its collision with a ball. The fifth means uses the bat speed before the collision with a ball obtained from the fourth means to obtain a mathematical equation for a batted ball speed after its collision with the bat. The sixth means plots a curve of the batted ball speed after collision with the bat versus the weight of the bat striking the ball.

It is desirable to provide a method and apparatus for generating a set of measurements which can be used to provide a set of standards for softball or baseball bats and other similar sports equipment that strike another piece of sports equipment such as a ball or hockey puck in order to insure fair play and unfair advantages in hitting power and unsafe flight times and speed of the ball or hockey puck for a sports game.

SUMMARY OF THE INVENTION

The present invention is directed to a technique for defining and determining the performance of a softball or baseball bat and similar sports equipment such as golf clubs, hockey sticks, and tennis rackets that strike another piece of sports equipment such as a ball or hockey puck during playing of a game.

Viewed from one aspect, the present invention is directed to a method of determining a performance of a first object comprising known characteristics of a Moment of Inertia, a weight, and a location of a Center of Mass. In a first step of the method, an impact is caused between the first object and a second object so as to cause the first object to rebound, the second object having known physical characteristics including a known Coefficient of Restitution and a predetermined velocity relative to the first object just before the impact. In a second step of the method, the velocity of the first object is measured during the rebound thereof from the impact. In a third step of the method, a Coefficient of Restitution between the first and second objects is determined using the rebound velocity of the first object measured in second step and the predetermined velocity of the second object. In a fourth step of the method, a performance factor for the first object is determined from the known characteristics of the second object and the Coefficient of Restitution between the first and second objects determined in third step.

Viewed from another aspect, the present invention is directed to a method of determining a performance of a first object comprising a known Moment of Inertia about a predetermined rotation point impacting a second object which has known characteristics including a known Coefficient of Restitution. In a first step of the method, the first object is rotatably mounted at the predetermined rotation point. In a second step of the method, the first and second objects are caused to have essentially non-spin impact so as to cause the first object to rotate and the second object to rebound after the impact. In a third step of the method, the velocity of the second object is measured relative to the first object before the impact of the two objects. In a fourth step of the method, the velocity of the first object is measured after impact with the second object. In a fifth step of the method, the Coefficient of Restitution between the first and second objects is determined using the measured velocities from the third and fourth steps. In a sixth step of the method, a performance factor for the first object is determined from the known characteristics of the second object and the Coefficient of Restitution between the first and second objects.

Viewed from still another aspect, the present invention is directed to a method of determining a performance of a first piece of sport equipment having a known Moment of Inertia (MOI) "I" about a predetermined axis of rotation thereof that is used to strike a second piece of sports equipment having a weight "w" and a predetermined Coefficient of Restitution (COR). In a first step of the method, the first piece of sports equipment is mounted at the predetermined axis of rotation thereof in a mounting means. The mounting means is arranged to freely rotate (e.g., using ball bearings) the first piece of sports equipment from a stationary predetermined starting position when the first piece of sports equipment is impacted substantially normal to a longitudinal axis thereof and substantially at a center of a predetermined impact area thereof by the second piece of sports equipment. In a second step of the method, the second piece of sports equipment is caused to be propelled with a velocity "v" at the center of the predetermined impact area of the first pice of sports equipment. In a third step of the method, the velocity "v" of the second piece of sports equipment is measured with a first measuring means. In a fourth step of the method, the velocity "V" of the first piece of sports equipment is measured with a second measuring means as the first piece of sports equipment rotates about its axis of rotation from being impacted by the second piece of sports equipment for determining (1) a Coefficient of Restitution (COR) between the first piece and the second piece of sports equipment, and (2) a performance factor of the first piece of sports equipment.

Viewed from still another aspect, the present invention is directed to a system for determining a performance of a first object comprising known characteristics comprising a Moment of Inertia, a weight, and a location of a Center of Mass, the system comprising impact causing means and measuring means. The impact causing means causes an impact between the first object and a second object so as to cause the first object to rebound, the second object having known physical characteristics including a known Coefficient of Restitution, and a predetermined velocity relative to the first object just before the impact. The measuring means measures the velocity of the first object during the rebound thereof from the impact such that a Coefficient of Restitution between the first object and second objects is determined, and a performance factor for the first object is determined from the known characteristics of the second object, the Coefficient of Restitution between the first object and second objects.

Viewed from still another aspect, the present invention is directed to a system for determining a performance of a first object comprising a known Moment of Inertia impacting a second object which has known characteristics including a known Coefficient of Restitution. The system comprises mounting means, non-spin impact means, first measuring means, and second measuring means. The mounting means rotatably mounts the first object such that the first object rotates when the first and second objects impact each other. The non-spin impact means causes the second object to have a non-spinning impact with the first object so as to cause the first object to rotate and the second object to rebound after impact. The first measuring means measures the velocity of the second object relative to the first object before the impact of the two objects. The second measuring means measures the velocity of the first object after impact with the second object so as to determine a performance factor for the first object.

Viewed from still another aspect, the present invention is directed to a system for determining the performance of a first piece of sport equipment having a known Moment of Inertia (MOI) "I" about a predetermined axis of rotation thereof that is used to strike a second piece of sports equipment with a weight "w" during the playing of a sports game. The system comprises mounting means and measuring means. The mounting means is used to mount the first piece of sports equipment at the predetermined axis of rotation thereof. Still further, the mounting means is arranged to freely rotate the first piece of sports equipment from a stationary predetermined starting position when the first piece of sports equipment is impacted substantially normal to a longitudinal axis thereof and substantially at a center of a predetermined impact area thereof by the second piece of sports equipment moving at a velocity "v". The measuring means is used to measure (a) the velocity "v" of the second piece of sports equipment propelled at the center of a predetermined impact area, and (b) the velocity "V" of the first piece of sports equipment as the first piece rotates about its axis of rotation after it has been impacted by the second piece of sports equipment. The measured quantities of "v" and "V" are used to determine a Coefficient of Restitution between the first piece and the second piece of sports equipment, and a performance factor for the first piece of sports equipment.

Viewed from still another aspect, the present invention is directed to a propulsion device for propelling an object placed therein. The propulsion device comprises a structure, a piston, accelerating means, and decelerating means. The structure has sidewalls which define a bore having a cross-section that is selected so as to facilitate movement of the object through a portion thereof. The piston is arranged for movement within the bore with a surface thereof having a contour shaped to cradle the object when the object is propelled out of the bore after being placed therein. The accelerating means causes the piston to be accelerated so as to cause the object to be cradled on the surface of the piston and propelled out of the bore without touching the sidewalls of the bore. The decelerating means subsequently causes the piston to be decelerated.

Viewed from still another aspect, the present invention is directed to a gas cannon for propelling an object placed therein. The gas cannon comprises a tube, first and second pistons, and a baffle. The tube has sidewalls which define a longitudinal bore, and an inlet port at a first end of the tube for selectively receiving a gas into the bore, the size of the bore being selected so as to allow the object to be placed therein. The first and second pistons are coupled together by a coupling member and are disposed within the bore of the tube for longitudinal movement. The the first piston is located closer to the inlet port than the second piston. The second piston comprises a major surface for cradling the object such that when the object is propelled from the bore the object does not touch the sides of the bore. The baffle comprises an outer surface which fixedly engages the surface of the bore of the tube at a predetermined location to divide the bore into two parts. The baffle defines an aperture through which the coupling member is able to move when the first piston is caused to move by the gas entering the inlet port of the tube.

The invention will be better understood from the following more detailed description taken with the accompanying drawings and claims.

DETAILED DESCRIPTIONS

It is to be understood that corresponding elements performing the same function in each of the figures have been given the same designation number.

Figure 1:
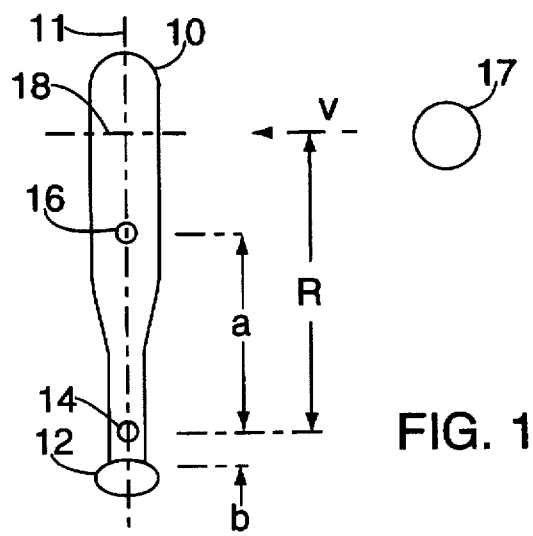
FIG. 1 is a top view of a softball bat for illustrating a concept of the present invention.

Referring now to FIG. 1, there is shown a top view of a softball bat (object or first object) 10 for illustrating a concept used in the present invention. It is to be understood that the softball bat 10 is used for illustrative purposes only, and that any other suitable first piece of similar sports equipment such as, for example, a baseball bat, a golf club, a hockey stick, or a tennis racket can be used in place of the bat 10. The softball bat 10 comprises a knob 12 at a first end of the bat 10, an axis of rotation 14 located at a distance "b" from the knob 12, a center of mass (CM) 16 located at a distance "a" from the axis of rotation 12, and a predetermined impact line 18 located at a distance "R" from the axis of rotation 12 where a softball (second object) 17 is aimed to centrally impact the bat 10.

In a ball game, a hitter accelerates the bat 10 by applying muscular forces and torques on a handle of the bat 10. The applied muscular forces cause the center of mass (CM) 16 to accelerate, and the applied torques cause the bat 10 to rotationally accelerate about its CM 16. Just as the mass of the bat 10 measures the resistance of the bat 10 to applied forces, the Moment of Inertia (MOI) of the bat 10 measures the resistance of the bat 10 to the applied torques. Since the motion of the bat 10 is primarily rotational, it is the MOI that determines how fast the bat 10 can be swung by a given hitter. When the MOI of the bat 10 increases, the speed of the bat 10 decreases.

The MOI of a rigid body (e.g., bat 10) about an axis is conventionally defined as the integral of the mass of the body weighted by the square of the distance to the axis. Typical units of MOI in the metric system are kg(meters)$^2$, and in English system are slug(ft)$^2$ or lb(ft)$^2$/(ft/s$^2$)= lb.ft.sec$^2$. Since the weights of bats 10 are usually measured in ounces and the length of bats are usually measured in inches, the present invention uses MOI's in units of oz.in$^2$. The axis of rotation 14 is a line through the center of the bat 10 that is perpendicular to a longitudinal axis 11 of the bat 10 at a predetermined distance "b" from an inside edge of the knob 12. For the present invention, the distance "b" is chosen as approximately 5.5 inches, but any other suitable distance can be chosen depending on the bat 10 or other similar sports equipment that is used. A typical value of the MOI of a softball bat 10 about this axis 14 of b=5.5 inches is about 9000 oz.in$^2$, and the CM 16 of such a bat 10 is typically about a distance a=15 inches from the axis of rotation 14, or 20.5 inches from the inside edge of the knob 12.

A typical or "standard" hitter can swing a bat 10 with an MOI of 9000 oz.in$^2$ with an angular speed of approximately 8 revolutions per second (rps). This speed increases to approximately 8.5 rps for a bat 10 with an MOI of 8000 oz.in$^2$, and decreases to about 7.5 rps for a bat 10 with an MOI of 11000 oz.in$^2$, with corresponding bat speeds of 78.5 and 64.1 miles per hour (MPH), respectively, found at a distance of two feet from the axis of rotation 14. Comparisons of performance characteristics among different bats 10 are made in reference to the "standard" hitter.

Given the weights of the bat 10 and a softball 17, the MOI of the bat 10, the velocity "v" of the ball 17, and a velocity "V" of the bat 10 at the point of impact at line 18, the remaining quantity that determines the rebound velocity "v'" of the hit ball 17 is the Coefficient of Restitution $e_f$ (COR $e_f$) between the ball 17 and the bat 10 at the point of impact along the impact line 18. A Coefficient of Restitution (COR) is defined as a measure of impact efficiency determined as the relative speed of the objects after impact divided by the relative speed of the objects before impact. Therefore, in the present circumstance, the quantity of the COR $e_f$ is defined as the ratio of the relative ball-bat velocity, perpendicular to the hit surface, after and before the collision between the ball 17 and the bat 10. The COR $e_o$ of the ball itself is the ratio v'/v of the rebound speed "v'" to the incident speed "v" of the ball 17 when the ball 17 is bounced perpendicularly off of a very heavy completely inelastic flat surface, as is discussed hereinafter in association with a performance measurement system shown in FIG. 2. The quantity of COR $e_o$ is relatively easy to measure and is required by many softball associations to generally have values between 0.47 and 0.51 for softballs.

The ball-bat COR $e_f$ is, however, difficult to measure when the bat 10 is unconstrained. In accordance with the present invention, a related "COR e" is to be measured which is defined as a ratio of relative speeds when the bat 10 is constrained to rotate about a fixed axis 14. Since the rebounding of the ball 17 off of the bat 10 occurs before the effects of the constraint of the bat 10 can influence the motion of the ball 17, this choice is reasonable, but it should be recognized the "COR e" is not necessarily the same as the conventional "COR $e_f$".

The softball bat 10 of FIG. 1 is considered to have an MOI=I and is constrained to rotate substantially without friction about the axis of rotation 14 at a distance "b" from the knob 12. When a softball 17 of a weight "w" moving at a speed "v" strikes the bat 10 in a central collision at a distance "R" from the axis of rotation 14, the softball ball 17 rebounds with a speed "v'" and the bat 10 acquires a rotational speed "v$^a$" (angular velocity) about the axis of rotation 14. The COR "e" between the ball 17 and the bat 10 at the distance R is determined from the Equation $$E = V + v'/v \qquad (1)$$

where V is the speed of the bat 10 at a distance R from the axis of rotation 14 and is equal to $$V = v^a R \qquad (2)$$

The three speeds of V, v, and v' are related by angular momentum conservation as follows:

$$wRv = I_r^a - wRv' \qquad (3)$$

Thus, from Equations (1), (2), and (3), $$v' = (IwR^2)V - v, \qquad (4)$$

and $$e = [1 + (I/wR^2)](V/v) - 1 \qquad (5)$$

Therefore, the "COR e" is primarily determined from the measurements of v and V.

Alternatively, an attempt can be made to measure the rebound velocity "v'" directly and use Equation (1) to evaluate "e". However, because the bat 10 starts to rotate during the impact with the ball 17, and because of the imperfect circular geometry of both the bat 10 and the ball 17, it is prohibitively difficult to accurate measure the relevant component of the ball rebound velocity "v'". The above described use of angular momentum conservation to evaluate the ball rebound velocity "v'", using the impact ball speed "v", the rebound bat speed "V", and the MOI "I" of the bat 10, completely circumvents the need to measure the ball rebound velocity "v'" and greatly increases the accuracy of the COR measurement.

The COR e is generally a function of the distance R, with a maximum value ê at some specific value $R^ê$ of R. Since a larger e provides a greater speed v' of a hit ball 17, a hitter should attempt to strike the ball 17 at a distance $R^ê$. There are, however, other criteria for choosing the best possible value of R, as, for example, a value of R which maximizes the energy transferred to the ball 17, a value of R which maintains the grip of the bat 10 at rest during collision between the bat 10 and the ball 17, and a value of R which does not excite a primary vibrational mode of the bat 10. Fortunately, these various values of R are rather close together. The COR also depends on the value of the speed V+v with which the ball 17 and the bat 10 approach each other.

In a realistic game situation in which, for example, a pitched ball 17 is hit with a swung bat 10, the velocity v' of the hit ball 17 is uniquely determined given the values of w (weight of the softball 17), W (weight of the bat 10), I (MOI of bat 10), v (velocity of the ball 17 prior to a collision with the bat 10), V (rotational speed of the bat 10 at a distance R from axis 14), and e (as determined from Equation 5). It is to be understood that if the ball 17 is rotating, or if a non-central impact occurs between the ball 17 and the bat 10, the effects of ball spin must also be considered. The present invention avoids such complicated calculations in the measurement of "e" by projecting the ball 17 centrally onto the bat 10 along the impact line 18 with substantially no spin on the ball 17. In turn, the rebound velocity v' of the hit ball 17 determines the trajectory of the hit ball 17 and the distance traveled. The forces of gravity and air resistance act on the ball 17 during its flight. If the ball is spinning there is also a "lift" or a "drop" force. The resultant trajectory and the range and flight-time of the hit ball 17 for any value of v' can be determined by any suitable means as, for example, using a computer. Limits on the range and flight-time of a hit ball 17 can, therefore, be implemented as limits on W, I and ê.

Figure 2:
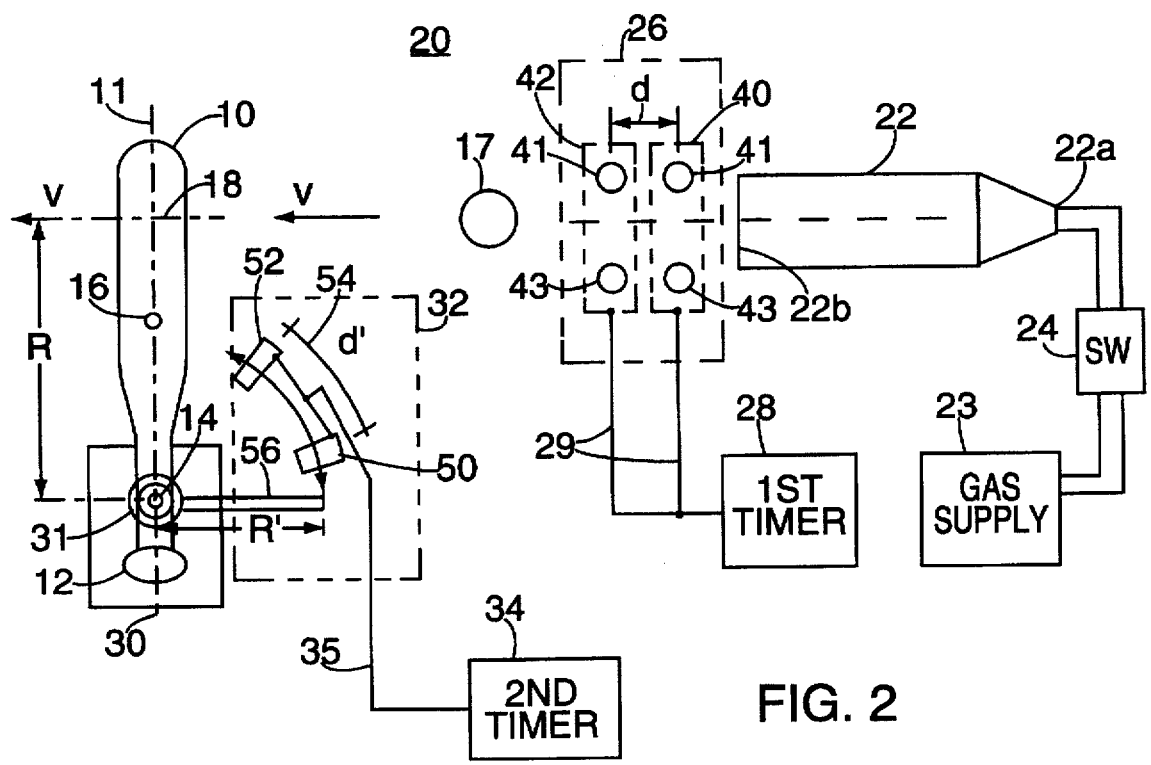
FIG. 2 is a performance measurement system in accordance with the present invention.

Referring now to FIG. 2, there is shown a performance measurement system 20 in accordance with the present invention which is shown with a bat (first object) 10 to be tested. It is to be understood that although the system 20 is hereinafter described for use in measuring the performance of softball bats, the concept of the system 20 can be used for measuring the performance of a first piece of sport equipment as, for example, a tennis racket, a golf club, or a hockey stick that is used to strike a second piece of sports equipment such as, for example, a ball or hockey puck.

The performance measurement system 20 comprises a gas cannon (propulsion device, means for causing non-spin impact) 22, a gas supply 23, a gas switch (SW) 24 coupling the gas supply 23 to a first end 22a of the cannon 22, a first measuring means 26 (shown within a dashed-line rectangle) coupled to a first timer 28, a turntable (mounting means) 30 comprising (a) a freely rotating shaft 31 on which the bat (object or first object) 10 can be fixedly mounted in a predetermined position in preparation for a test thereof, (b) a traveler arm 56 mounted on the shaft 31, and (c) a second measuring means 32 (shown within a dashed-line rectangle) coupled to a second timer 34. The gas supply 23 comprises a regulator (not shown) for raising or lowering the pressure of the gas supplied by the gas supply 23 to a predetermined pressure. The gas switch 24 is selectively operable to permit gas at the predetermined pressure from the gas supply 23 to enter the first end 22a of the gas cannon 22. In turn, the predetermined gas pressure causes the gas cannon 22 to operate and propel the ball (second object) 17 with substantially no spin on it so that it centrally strikes the bat 10 with a predetermined velocity "v". The gas cannon 22 is preferably a device that is capable of, for example, shooting or propelling a ball 17 at a speed of, for example, 88 ft./sec. with a maximum aiming error of ±0.125 inch (6 mm.) at a point of impact with the softball bat 10 along impact line 18. For realistic conditions with baseball bats, high speeds of, for example, 200 ft./sec. are necessary to determine baseball bat CORs. Still further, the exhaust gas from the gas cannon 22 must not pass to the bat 10, and the gas cannon 22 can be placed at any distance from the impact location of the bat 10 so long as the cannon 22 can meet reasonable ball aim and repeatability requirements. It is to be understood that the gas used by the gas cannon 22 can comprise any suitable gas, and is preferably air or Nitrogen ($N_2$).

Figure 3:
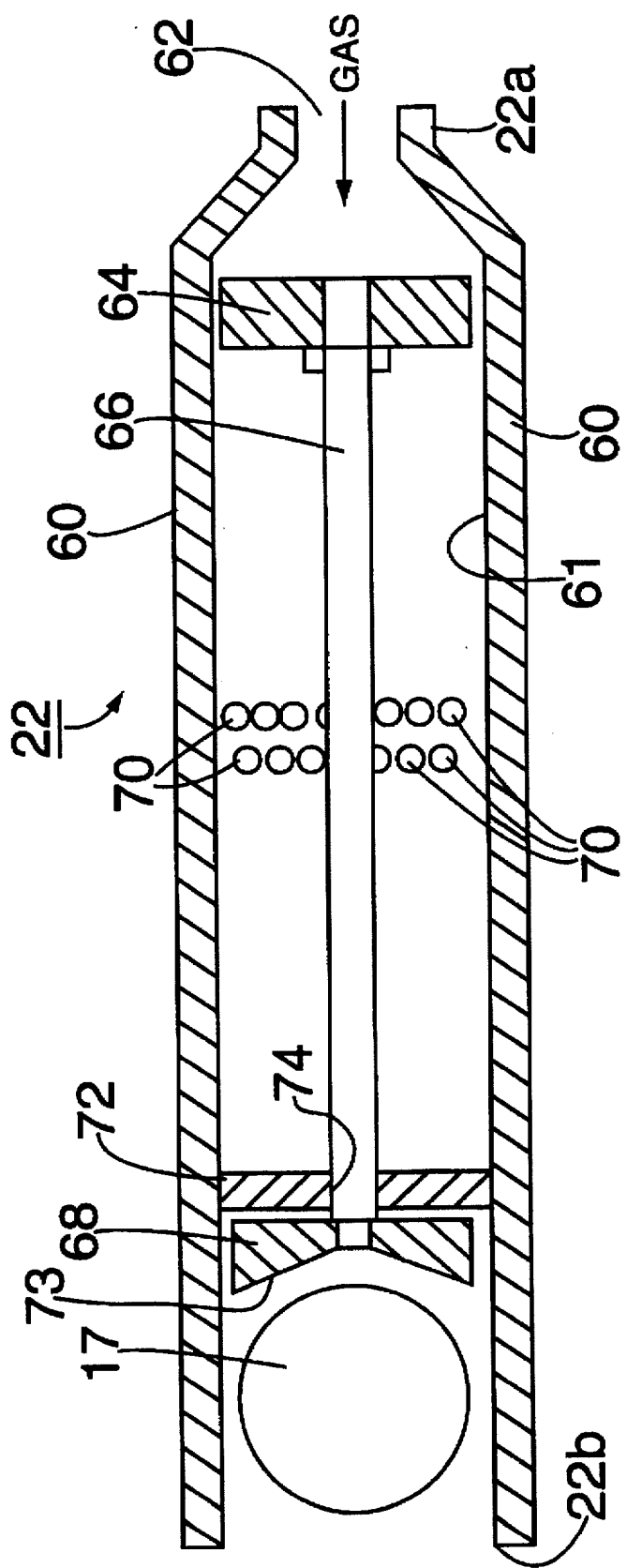
FIG. 3 is a cross-sectional side view of an air cannon for projecting a ball at a bat in the performance measurement system of FIG. 2 in accordance with the present invention.

Referring now to FIG. 3, there is shown a cross-sectional view of a novel gas cannon (propulsion device) 22, in accordance with the present invention, that propels a ball (a second object, a second piece of sports equipment, an object) 17 with substantially no spin thereon for use in the performance measurement system 20 of FIG. 2. The gas cannon 22 is formed from a cylindrical tube (structure) 60 which defines a circular bore 61 and a plurality of apertures 70 surrounding a predetermined portion of the tube 60. The gas cannon 22 comprises a gas inlet port 62 at one end of the bore 61 for introducing a gas (e.g., air) under a predetermined pressure from a gas supply 23 (shown only in FIG. 2) into the bore 61, a first piston section 64 and a spaced-apart second piston section 68 which are coupled together (typically fixedly interconnected) by a coupling member (rod) 66, and a baffle (separator member) 72 disposed between the first and second pistons 64 and 68 and between the apertures 70 and the second piston 68 for dividing the bore 61 into first and second portions. The baffle 72 defines a central aperture 74 through which the rod 66 extends. The second piston 68 has a cone shaped end 73 for engaging a ball 17 to be propelled from the gas cannon 22. In the gas cannon 22, the first piston 64, the rod 66, the second piston 68, and a portion of the sidewalls of the bore 61 form an accelerating means, and the first piston 64, the baffle 72, and a portion of the sidewalls of the bore 61 form a decelerating means.

In operation, the first and second pistons 64 and 68 and the rod 66 are moved as far as possible towards the gas inlet port 62, and a ball 17 is inserted into the bore 61 to engage the second piston 68. At this time the second piston 68 is preferably very close to the baffle 72, and the apertures 70 defined in the cylindrical tube 60 are slightly closer to the first piston 64 than they are to the baffle 72. Gas at a predetermined pressure is then forced through the gas inlet 62 by the operation of a gas switch 24 (shown only in FIG. 2). The pressurized gas causes the first piston 64 (along with the rod 66 and the second piston 68) to accelerate away from the gas inlet port 62 towards the baffle 72. This, in turn, causes the second piston 68 to cradle and push the ball 17 centrally out of a second end 22b of the gas cannon 22 at a predetermined velocity "v" without the ball 17 hitting the sides of the bore 61 of the gas cannon 22 due to the cone-shaped end 73 of the second piston 68. The apertures 70 permit gas to move out of the bore 23 during an acceleration phase as the first piston 64 moves within the bore 61 towards the area of the apertures 70. Once the first piston 64 moves past the area of the apertures 70, gas can no longer escape from the bore 61 and the gas remaining in the bore 61 is compressed between the first piston 64 and the baffle 72 to quickly decelerate and the motion of the first and second pistons 64 and 68 to a stop before the first piston 64 engages the baffle 72. In this manner, the gas cannon 22 is able to propel the ball 17 towards the bat 10 (shown in FIG. 2) with substantially no spin on the ball 17, thereby effectively eliminating any need to consider ball spin in any of the required calculations. It is to be understood that any other suitable means can be used instead of the gas to accelerate the first and second pistons 64 and 68 as, for example, a spring, an electrically accelerated shaft, a rotating drum, or similar device. Still further, it is to be understood that any other suitable means can be used instead of the gas compressed between the first piston 64 and the baffle 72 to decelerate the first piston 64 so it does not strike the baffle 72 as, for example, one or more chains, springs, an electric brake, a counter weight, or similar device. Alternatively, the apertures 70 through the tube 60 can be eliminated and apertures (not shown) can be formed through the baffle 72 that are opened during the acceleration phase of the first and second pistons 64 and 68, and are closed by covering means (not shown) when the first piston 64 reaches a predetermined point within the bore 61. Sensing means (not shown), which is coupled to the covering means, can be used to determine when the first piston 64 reaches the predetermined point. The sensing means then sends a signal to the covering means to cause the apertures in the baffle 72 to be closed. Gas between the first piston 64 and the baffle 72 becomes compressed and acts to decelerated movement of the first and second pistons 64 and 68.

Returning now to FIG. 2, the first measuring means 26 is disposed between a second end 22b of the gas cannon 22 and the bat 10 and comprises a first optical detecting means 40 (shown within a dashed-line rectangle), and a second optical detecting means 42 (shown within a dashed-line rectangle) which is spaced-apart from the first optical detecting means 40 by a distance "d". Each of the first and second optical detecting means 40 and 42 comprises a separate light source 41 for directing a narrow or pencil light beam (not shown) onto an associated light sensor 43. The first and second optical detecting means 40 and 42 can comprises any suitable device such as a light trap, or an equivalent device, capable of, for example, measuring an edge of an object traveling at speed in excess of 88 ft./sec. (26.8 m/s) with an accuracy of 0.5 fps (0.2 m/s) or better. The first and second optical detecting means 40 and 42 should be capable of measuring, for example, across a length of no less than one-half of the diameter of the ball 17 to avoid edge effects. For example, when testing softball bats 10 with softballs 17, the first and second optical detecting means 40 and 42 should sense an object passing nearby across at least a two inch (5 cm.) line.

The light sensor 43 of the first optical detecting means 40 triggers the first timer 28 to start its timing cycle when the ball 17 is a predetermined distance from the bat 10. For example, the first optical detecting means 40 is located to trigger the first timer 28 to start its timing cycle when the ball is no more than twelve inches (30.5 cm.) from the surface of the bat 10. In turn, it is suggested that the light sensor 43 of the second optical detecting means 42 triggers the first timer 28 to stop its timing cycle when the ball 17 is, for example, between 6 inches (15.24 cm.) and 9 inches (22.86 cm.) from the surface of the bat 10 to most accurately measure the velocity "v" of the ball adjacent to the surface of the bat 10.

In operation, the ball 17 is propelled from the second end 22b of the gas cannon 22 and passes between each of the associated light sources 41 and light sensors 43 of each of the first and second optical detecting means 40 and 42 in sequence. As the ball 17 passes between the light source 41 and light sensor 43 of the first optical detecting means 40, it momentarily blocks the light beam from the light source 41 and causes the first timer 28 to start its timing cycle. When the ball 17 passes between the light source 41 and light sensor 43 of the second optical detecting means 40, it momentarily blocks the light beam from the light source 41 and causes the first timer 28 to stop its timing cycle and provide a total elapsed time having a measured value of "T". From such measured value of "T", and knowing the precise distance "d" between the first and second optical detecting means 40 and 42, the velocity "v" of the ball 17 propelled by the gas cannon 22 near the surface of the bat 10 is determined by the Equation $$v=d/T. \quad (6)$$

A calibration procedure described hereinbelow makes it unnecessary to precisely measure the value of "d".

The turntable 30 comprises (a) a freely rotating shaft 31 comprising clamps (not shown) that fixedly mount and align the bat 10 onto the shaft 31 and in the path of the ball 17 propelled by the gas cannon 22 at any chosen impact distance "R", (b) a rigid traveler arm 56 mounted on the shaft 31, and (c) a second measuring means 32 (shown within a dashed-line rectangle) coupled to a second timer 34. The rotating clamps and shaft 31 assembly should preferably not weigh more than, for example, three pounds (1.362 kg.) and should be able to spin freely on ball bearings. The Polar Moment of Inertia for the clamp turntable assembly preferably should not exceed, for example, 100 oz.in$^2$. The rigid traveler arm 56 is fixedly attached to the freely rotating shaft 31 and extends outwards perpendicular to the longitudinal axis (not shown) of the shaft 31 for a distance "R'" and forms a part of the turntable 30 and the second measuring means 32. The second measuring means 42 comprises a first gate 50 and a second gate 52 that are spaced apart at a distance "d'" along the rotational path of an end of the traveler arm 56 opposite the end that is fixedly attached to the shaft 31. Alternatively, light sources and sensors can be used in the second measuring means 42 in the manner shown and described for the first measuring means 26.

In operation, when the ball 17 perpendicularly and centrally impacts the stationary bat 10 at a distance "R" from both the axis of rotation 14 of the bat 10 and the shaft 31, the bat 10 is caused to move around its axis of rotation 14 with a velocity "V" at the distance "R" by the impact of the ball 17. The rotation of both the bat 10 and the shaft 31 causes the rigid traveler arm 56, which is fixedly attached to the shaft 31, to rotate past the first and second gates 50 and 52 in sequence. As the traveler arm 56 reaches the first gate 50, it trips the first gate 50 and causes the first gate 50 to send an electrical signal to the second timer 34 to start a timing cycle. As the traveler arm 56 reaches the second gate 52, it trips the second gate 52 and causes the second gate 52 to send an electrical signal to the second timer 34 to stop the timing cycle. The second timer 34, therefore, provides reading of a total elapsed time having a measured value of "T'" for the traveler arm 56 to travel the distance "d'" corresponding to the spacing between the first and second gates 20 and 52. The angular speed "v$^a$'" of the bat 10 after the collision with the ball 17 is equal to $$v''' = d'/RT', \tag{7}$$

where "d'" is the distance between the first and second gates 50 and 52, R' is the length of the traveler arm 56, and T' is the time measured by the second timer 34.

From the concept of angular momentum conservation, the ball 17 rebounds from the impact with the bat 10 at a velocity "v'" as expressed by the Equation $$v' = (Iv''/wR) - v, \tag{8}$$

where I is the Moment Of Inertia (MOI) of the bat 10 about the axis of rotation 14, and w is the weight of the ball 17, and R is the distance between the axis of rotation 14 and the impact line 18 of the bat 10. The Coefficient of Restitution (COR) of the bat 10 at the distance R can then be determined from the Equation $$e = [1 + I/wR^2](d'RT/dR'T') - 1. \tag{9}$$

It is to be understood that official softballs 17 that are approved for play are marked with a Coefficient of Restitution (COR) and a compression from a previously run test. Each individual ball 17 used in the present test is preferably to be marked with the actual tested and verified ball COR obtained when tested in accordance with the well-known American Society of Testing Materials (ASTM) standard TBD. Such ASTM Standard TBD softball standards include the values of (a) compression (e.g., 130±5 lbs. at ¼ inch deflection), (b) Weight (e.g., 185±6 grams), (c) Size (e.g., 11.5±0.125 inches circumference), and (d) COR [e.g., 0.47±0.005 (0.465–0.475)].

The features of each bat 10 are determined by preferably first measuring the weight "W" of the bat 10 to the nearest 0.01 ounce, and determining the balance point (BP) of the bat 10. To obtain the BP, the bat 10 is balanced over a pin with a maximum radius of, for example, one-sixteenth inches (1.58 mm) so that the longitudinal axis 11 of the bat 10 is parallel to the horizon. The distance from the rotation point 14 to the center of the radius on which the bat is balancing is measured and recorded, and is referred to as the BP.

The hereinabove described COR measurement procedure is appropriate for any value of the impact distance "R" from R=0 (the pivot point location 14) to R=L (the end location of the bat 10). There is, however, a preferred value of R. When R has a value that is located at the Center of Percussion (COP) of the bat 10 relative to the pivot point 14, then the impact of the ball 17 on the bat 10 produces no reaction at the pivot point 14. Therefore, the bat 10 then acts as a free body, just as the bat 10 does when used by a hitter in a ball game. The reason for this is that when a free bat 10 at rest is struck by a ball 17, the center of mass (balance point BP) of the bat 10 will in general move straight back and the entire bat 10 will simultaneously rotate about the BP. There is one impact point, the COP, where these two motions cancel exactly at the chosen pivot point 14 location. The impacted clamped bat 10 then reacts as if the clamp were not present, and the COR measured by the procedure described hereinabove at the COP is the same COR value that is relevant when the ball 17 is hit at the COP of the bat 10 by a human hitter. Still further, the COP of the bat 10 is very near other "sweet spots" of the bat 10: the maximum energy transfer point, the maximum of the COR, and the node of the first vibrational mode.

The second step is to determine the "Center of Percussion" (COP) of the bat 10, which is also known as the center of oscillation, where forces and impacts do not introduce reactions at a pivot point of the bat 10. The COP determination is made by applying a collar or clamp to the handle end of the bat 10 where the pivot point is located, for example, 5.5 inches (13.97 cm) from the innermost end of the knob 12 of the bat 10. The bat 10 is then hung vertically in a stand making sure that the bat 10 hangs squarely and can swing freely on a knife-edge attached to the clamp about its pivot point. In the COP test, the bat 10 is rotated about the pivot point at some angle less than, for example, 10° from vertical. The bat 10 is released and allowed to swing freely through approximately 5 cycles and settle into a simple pendulum oscillation. At this time a timer such as a stop watch or other suitable means is started when the bat 10 reaches either end of a swing cycle and is stopped once the bat 10 has completed, for example, ten full cycles. It is preferred that this test be repeated a number of times (e.g., 10 times) to minimize timing errors. Results which vary more than, for example, 2% should not be used, and, if such variations occur, the bat 10 should be retested after verifying that the bat 10 is securely and properly centered at the pivot point and swings freely. The average period of the bat 10 is then determined and recorded by adding the values of the measured time divided by the number of cycles for each test divided by the number of tests. This average period "t" is then used to determine the bat COP location "c" by the equation $c = (t/2\pi)^2 g$, where $g = 32$ ft./sec$^2$ or 9.8 m/sec$^2$ and is the acceleration of gravity. In English (inches) or Metric units (centimeters) relative to the exemplary 5.5 inch (13.97 cm) pivot point, the COP is given by either of the Equations $$\text{COP (in)} = (\text{Avg. Period})^2 \ (9.779 \text{ in/sec}^2), \text{ or}$$

$$\text{COP (cm)} = (\text{Avg. Period})^2 \ (24.839 \text{ cm/sec}^2). \tag{10}$$

The Moment of Inertia (MOI) of a bat 10 with a weight "W" can also be determined and recorded in English or Metric units, relative to the exemplary 5.5 inch (13.97 cm) pivot point, by the equation I=Wac, where "a" is the distance between the pivot point and the BP. The MOI "I" is, therefore, given by the following Equations $$I \ (\text{oz.in}^2) = (\text{Avg. Period})^2 \ (9.779) \ [W(BP-5.5)], \text{ or}$$

$$I \ (\text{g.cm.}^2) = (Av_g. \text{ Period})^2 \ (24.839) \ [W(BP-13.97)]. \tag{11}$$

Prior to running tests, the performance measurement system 20 is initially calibrated by installing a very heavy "block" bat 10 (e.g., at least 30,000 oz.in$^2$) on the turntable 30, where the "block" bat 10 has a flat surface where the ball 17 impacts the "block" bat 10. Because of the finite size and variable sensitivity of the light sensors 43 and the resultant impossibility of accurately measuring the distances between the sensors, it is virtually impossible to accurately measure the ratio of d'/dR', where d' is the distance between the first and second bat speed gates (sensors) 50 and 52, d is the distance between the ball speed sensors of the first and second optical detecting means 40 and 42, and R' is the distance of the traveler arm 56 between the bat pivot center 14 and the first and second bat speed gates (sensors) 50 and 52. The value of this ratio is needed to determine the bat-ball COR. To precisely determine this ratio in accordance with the present invention, it is proved that by using a very heavy flat surfaced "block" bat 10, the bat-ball COR is equal to just the ball COR. More particularly, by striking a "block" bat 10 of a known large MOI=$I_o$ with a ball 17 of a known COR=$e_o$ and weight $w_o$ at a distance $R_o$ from the pivot point 14 of the very heavy bat 10, and measuring the flight time $T_o$ of the incident ball 17 and the flight time "To'" of the very heavy bat 10 between the relative gates 50 and 52, the value of the ratio is determined from the Equation $$d'/dR' = (1+e_o)/[(R_o + I_o/w_o R_o)(T_o/T_o')]. \tag{12}$$

From the value of d'/dR' found in Equation 12, the ball-bat COR "e" for a bat 10 of MOI=I and a ball 17 of weight "w" striking the bat 10 at a distance R is then determined from the Equation $$e = (R + I/Rw)(d'/dR')(T/T') - 1 \tag{13}$$

in terms of the accurately measured values of R, I, w, T, and T'.

Once the performance measurement system 20 is initially calibrated as described hereinabove, the full procedure for the testing of bats 10 includes the following steps. The balls 17 and any wooden bats 10 to be used for testing are stored at test environmental conditions for a first predetermined period of time (e.g., 24 hours) prior to testing. Non-wood bats are stored at the test environmental conditions for a second predetermined period of time (e.g., 2 hours) prior to testing. Typical test environment conditions are, for example, a temperature of 72°±2° Fahrenheit or 22°±1° Celsius, and a relative humidity of 50%±5%. Once a ball 17 and a bat 10 are removed from such test environment conditions, they should be used for a test, for example, within one hour at similar temperature conditions and humidity conditions of from 20–60%. To prepare for a test, the weight and verified COR of a selected ball 17 are recorded. The gas cannon 22 is aligned, for example, by using lasers to squarely hit a flat plate bat 10 placed at the desired bat impact area 18.

The bat 10 to be tested is then mounted in clamps on the shaft 31 of the turntable 20 at the axis of rotation (pivot point) 14. The center of a barrel of the bat 10 is centered to the reference pin impact location by rotating the bat about its handle in the clamps at the pivot point 14. The impact of the ball 17 must be centered vertical to the longitudinal axis 11 of the bat 10, and horizontally at the previously measured Center of Percussion (COP), or any other chosen impact distance R, at the impact center line 18 of the bat. The bat 10 is then positioned against a start position reference (not shown) which places the longitudinal axis 11 of the bat 10 perpendicular to the line of travel of the ball 17. At this time the first and second timers 28 and 34 are reset and ready to take data.

The ball 17 is propelled from the gas cannon 22, and the travel time "T" of the ball 17 is recorded via the first measuring means 26 and the first timer 28. The speed (v=d/T) of the ball 17 is a specified range [e.g., 85 ft/sec (25.9 m/sec) to 91 ft/sec (27.7 m/sec)]. Concurrent therewith, with resultant travel time "T'" of the bat 10 is measured by the second measuring means 32 and the second timer 34. The bat-ball Coefficient of Restitution (COR) is determined using Equation (9).

The bat-ball COR e will, in general, depend on the ball COR $e_o$ used in the measurement. This makes it difficult to compare different bats 10 measured with different balls 17. It is, therefore, desirable to define a performance measurement which depends on the bat 10 alone, i.e., a quantity that is, to a good approximation, independent of the ball 17. It can be shown that such a quantity is obtained by dividing the bat-ball COR e by the ball COR $e_o$ used in the test. The ratio $e/e_o$, the Bat Performance Factor (BPF), thus characterizes the performance of the bat 10 itself. It is important to use balls 17 of a standard compression. The bat performance factor (BPF) for each test is determined using the Equation $$BPF = [(1 + I/wR^2)(d'/dR')(RT/T') - 1]/(\text{Ball COR } e_o), \tag{14}$$

where d'/dR' is the value determined from Equation (12). Then, the averaged BPF for the test bat 10 is determined by calculating the average bat performance results for a predetermined multiple bat-ball COR events (e.g., 6). If different balls 17 are used to test a same bat 10, the results should always be determined using the actual weight "w" of the ball 17 used in each of the multiple tests. The test balls must have a standard compression.

A batted ball speed "v*" resulting from a straight line collision between a pitched ball and a swung bat can be related to the BPF in accordance with the Equation $$v = [V(1+e) + v(e-k)]/(1+k), \tag{15}$$

where V is the measured speed of the bat 10 at the impact point, v is the measured speed of the ball 17 prior to contacting the bat 10, e is the bat-ball COR "e" (at a speed V+v) which is equal to the BPF multiplied by the COR of the ball 17, and k is a ball-bat inertia ratio. The ball-bat inertia ratio "k" is determined from the Equation $$k = (w/W) + [w(R-a)^2]/(I - Wa^2), \tag{16}$$

where w is the weight of the ball 17, W is the weight of the bat 10, R is equal to the distance between the pivot point and the Center of Percussion (COP) (or any other impact point) for the bat 10 where a typical value for an average bat 10 is 22 inches, a is equal to the distance between the pivot center 14 and the Center of Mass (CM) 16 of the bat 10, and I is equal to the Moment of Inertia (MOI) of the bat 10.

It is to be understood that, for purposes of Equation (15), the bat swing speed "V" in miles per hour (mph) is measured at the point of impact for which the bat-ball COR is e. It is best to impact the ball 17 at the "sweet spot" of the bat 10 where the resulting highest batted (rebounding) ball speeds due to the optimization of momentum transfer occurs. The BPF value can be measured at this point and represents the maximum performance of the bat 10. This "sweet spot" location in general depends on the batter's swing speed and on the speed and weight of the pitched ball, but it is generally very close to the COP. If the impact is at the COP, the calculation for Equation (15) is correct only when the bat swing speed (V) at the COP point impact is used. The bat swing speed (V) at the COP can be as much as 20% slower than bat speeds measured at the end of the bat 10 opposite the knob 12. Typical adult values of bat speeds are 60 mph for average players and 70 mph for top level softball players. It is to be understood that the bat swing speed of softball players varies depending on the skill level and conditioning of each player, and the bat swing weight (MOI).

It is to be appreciated and understood that the specific embodiments of the invention described hereinbefore are merely illustrative of the general principles of the invention. Various modifications may be made by those skilled in the art which is consistent with the principles set forth. For example, the present invention has been described in the form of a bat performance measuring system 20. However, any other piece of sports equipment such as a golf club, tennis racket, or hockey stick, that is used to strike another piece of sports equipment such as a ball or puck, can be tested in a similar manner depending on the standards for such pieces of sports equipment using the principles set forth for the present invention. Still further, the system 10 depicts the bat 10 being mounted for free rotation about the pivot point 14. It is to be understood that the bat 10 can alternatively be mounted in any other suitable mounting device where the entire bat 10 translates or is pushed backwards without rotation about an axis when impacted by the ball 17.

What is claimed is:

1. A method of determining a performance of a first object comprising known characteristics of a Moment of Inertia, a weight, and a location of a Center of Mass, the method comprising the steps of:

(a) causing an impact between the first object and a second object so as to cause the first object to rebound, the second object having known physical characteristics including a known Coefficient of Restitution, and a predetermined velocity relative to the first object just before the impact;

(b) measuring the velocity of the first object during the rebound thereof from the impact;

(c) determining a Coefficient of Restitution between the first and second objects using the rebound velocity of the first object measured in step (b) and the predetermined velocity of the second object; and (d) determining a performance factor for the first object from the known characteristics of the second object and the Coefficient of Restitution between the first and second objects determined in step (c).

2. The method of claim 1 further comprising the steps of:

(e) prior to performing step (a), rotatably mounting the first object for free rotation in a predetermined plane; and (f) in performing step (a), causing the second object to impact the first object normal to an axis of rotation of the first object in the predetermined plane of rotation and in a predetermined impact area of the first object.

3. The method of claim 1 wherein in step (a) causing the second object to have a substantially non-spin impact on the first object.

4. The method of claim 1 further comprising the step of:

(e) prior to performing step (d), determining the rebound velocity of the second object after impact with the first object in a game condition.

5. A method of determining a performance of a first object comprising a known Moment of Inertia about a predetermined rotation point impacting a second object which has known characteristics including a known Coefficient of Restitution, the method comprising the steps of:

(a) rotatably mounting the first object at the predetermined rotation point;

(b) causing the first and second objects to have essentially non-spin impact so as to cause the first object to rotate and the second object to rebound after the impact;

(c) measuring the velocity of the second object relative to the first object before the impact of the two objects;

(d) measuring the velocity of the first object after impact with the second object;

(e) determining the Coefficient of Restitution between the first and second objects using the measured velocities from steps (c) and (d); and (f) determining a performance factor for the first object from the known characteristics of the second object and the Coefficient of Restitution between the first and second objects.

6. A method of determining a performance of a first piece of sports equipment having a Moment of Inertia "I" about a predetermined axis of rotation thereof that is used to strike a second piece of sports equipment having a weight "w" and a predetermined Coefficient of Restitution comprising:

(a) mounting the first piece of sports equipment at the predetermined axis of rotation thereof in a mounting means, the mounting means being arranged to allow the first piece of sports equipment to freely rotate from a stationary predetermined starting position when the first piece of sports equipment is impacted substantially normal to a longitudinal axis thereof and substantially at a center of a predetermined impact area thereof by the second piece of sports equipment;

(b) causing the second piece of sports equipment to be propelled with a velocity "v" at the center of the predetermined impact area of the first piece of sports equipment;

(c) measuring the velocity "v" of the second piece of sports equipment with a first measuring means; and (d) measuring the velocity "V" of the first piece of sports equipment with a second measuring means as the first piece of sports equipment rotates about its axis of rotation from being impacted by the second piece of sports equipment for determining a Coefficient of Restitution between the first piece of sports equipment and the second piece of sports equipment, and a performance factor of the first piece of sports equipment.

7. The method of claim 6 wherein a rebound velocity "v'" of the second piece of sports equipment is determined from the expression $v'=(IV^a/wR)-v$, where $V^a$ is the angular speed of the first piece of sports equipment measured at a radial distance R' over a distance d' for a time T' after the first piece of sports equipment is impacted by the second piece of sports equipment, I is the Moment Of Inertia of the first piece of sport equipment about its axis of rotation, w is the weight of the second piece of sports equipment, and R is the distance between the axis of rotation of the first piece of sport equipment and the impact point of the second piece of sports equipment on the first piece of sports equipment.

8. The method of claim 6 further comprising the steps of:

(e) in performing step (c), measuring the time T that it takes for the second piece of sports equipment to travel a first predetermined distance "d" in order to determine the velocity "v"; and (f) in performing step (d), measuring the time T' that it takes for the first piece of sports equipment to radially travel a second predetermined distance "d'" at a third predetermined radial distance "R'" after the first piece of sports equipment is impacted with the second piece of sports equipment in order to determine the velocity "V".

9. The method of claim 8 further comprising the steps of:

(g) prior to performing step (a), making a test calibration by mounting a correspondingly-shaped first piece of sports equipment which has a predetermined weight= $W_o$ and a predetermined Moment of Inertia= $I_o$ at its predetermined axis of rotation thereof in the mounting means, where the predetermined weight $W_o$ of the correspondingly-shaped first piece of sports equipment is at least three times heavier than the weight W of the first piece of sports equipment to be tested and a surface of the correspondingly-shaped first piece of sports equipment is flat and incompressible where the second piece of sports equipment having a weight= $w_o$ and a Coefficient of Restitution= $e_o$ impacts the correspondingly-shaped first piece of sports equipment;

(h) performing step (c) to measure a time $T_o$ for the second piece of sports equipment to travel the first predetermined distance "d", while concurrently performing step (c) to measure a time "$T'_o$" for the correspondingly-shaped first piece of sports equipment impacted at a distance= $R_o$ from its predetermined axis of rotation to radially travel a second predetermined distance=d' at a third predetermined radial distance=R' from its predetermined axis of rotation; and (i) determining the ratio d'/dR' from the expression $d'/dR'=(1+e_o)/[(R_o+I_o/w_oR_o)(T_o/T'_o)]$.

10. The method of claim 9 further comprising the step of:
(j) determining a performance factor "PF" for the first piece of sports equipment to be tested that has an Moment of Inertia=I and is impacted at a distance "R" from its axis of rotation by the second piece of sports equipment having a weight=w and a predetermined Coefficient of Restitution=e from the expression $$PF=[(1+I/wR^2)(d'/dR')(RT/T')-1]/e_o.$$

11. The method of claim 6 wherein the second piece of sports equipment is a ball and in performing step (b) propelling the ball with substantially no spin thereon at the center of the predetermined impact area of the first piece of sports equipment.

12. A system for determining a performance of a first object comprising known characteristics comprising a Moment of Inertia, a weight, and a location of a Center of Mass, the system comprising:

impact causing means for causing an impact between the first object and a second object so as to cause the first object to rebound, the second object having known physical characteristics including a known Coefficient of Restitution, and a predetermined velocity relative to the first object just before the impact; and measuring means for measuring the velocity of the first object during the rebound thereof from the impact such that a Coefficient of Restitution between the first object and the second object can be determined, and a performance factor for the first object can be determined from the known characteristics of the second object and the Coefficient of Restitution between the first object and second objects.

13. The system of claim 12 further comprising:

means for rotatably mounting the first object for free rotation in a predetermined plane; and the impact causing means causes the second object to impact the first object normal to an axis of rotation of the first object in the predetermined plane of rotation and in a predetermined impact area of the first object.

14. The system of claim 12 wherein the impact causing means causes the second object to have a substantially non-spin impact with the first object.

15. The system of claim 12 further comprising means for determining the rebound velocity of the second object after impact with the first object in a game condition.

16. A system for determining a performance of a first object comprising a known Moment of Inertia impacting a second object which has known characteristics including a known Coefficient of Restitution, the system comprising:

mounting means for rotatably mounting the first object such that the first object will rotate when the first and second objects impact each other;

means for causing the second object to have a non-spinning impact with the first object so as to cause the first object to rotate and the second object to rebound after impact;

first measuring means for measuring the velocity of the second object relative to the first object before the impact of the two objects; and second measuring means for measuring the velocity of the first object after impact with the second object so as to determine a performance factor for the first object.

17. A system for determining a performance of a first piece of sports equipment having a known Moment of Inertia "I" about a predetermined axis of rotation thereof that is used to strike a second piece of sports equipment having a weight "w" during the playing of a sports game comprising:

mounting means for mounting the first piece of sports equipment at the predetermined axis of rotation thereof, the mounting means being arranged to freely rotate the first piece of sports equipment from a stationary predetermined starting position when the first piece of sports equipment is impacted substantially normal to a longitudinal axis thereof and substantially at a center of a predetermined impact area thereof by the second piece of sports equipment moving at a velocity "v"; and measuring means for measuring (a) the velocity "v" of the second piece of sports equipment propelled at the center of a predetermined impact area, and (b) the velocity "V" of the first piece of sports equipment as the first piece of sports equipment rotates about its axis of rotation after it has been impacted by the second piece of sports equipment for determining a Coefficient of Restitution between the first piece of sports equipment and the second piece of sports equipment, and for determining a performance factor for the first piece of sports equipment.

18. The system of claim 17 further comprising propelling means for propelling the second piece of sports equipment at the velocity "v" and aimed substantially at the center of the predetermined impact area of the first piece of sports equipment to be measured.

19. The system of claim 18 wherein the second piece of sports equipment is a ball and the propelling means is a gas cannon that propels the ball with substantially no spin thereon at the center of the predetermined impact area of the first piece of sports equipment to be measured.

20. The system of claim 19 wherein the gas cannon comprises:

a tube defining each of a cylindrical longitudinal bore that cross-sectionally substantially matches an outer shape of the ball to be propelled therefrom, an inlet port at a first end thereof for selectively receiving a gas at a predetermined pressure into the bore, and a plurality of apertures disposed around a predetermined portion of the tube, the tube having a circumference selected to house the ball therein prior to being propelled from the gas cannon;

first and second pistons being coupled together by a coupling member and being disposed within the bore of the tube for longitudinal movement with the first piston being located closer to the inlet port than the second piston, the second piston comprising a major surface for cradling the ball without the ball touching a surface of the bore when the ball is propelled from the bore;

a baffle comprising an outer surface which fixedly engages the surface of the bore of the tube at a predetermined location between the apertures defined in the predetermined portion of the tube and the second piston to divide the bore into two parts, the baffle defining an aperture through which the coupling member is able to move when the first piston is caused to move by the gas entering the inlet port of the tube; and the plurality of apertures being disposed so as to facilitate the escape of any gas in the bore of the tube between the baffle and the first piston while the first piston is located between the inlet port and the plurality of apertures, and for facilitating the escape of gas introduced into the inlet port when the first piston is between the plurality of apertures and the baffle.

21. The system of claim 19 wherein the propelleing means comprises:

a structure having sidewalls which define a bore having a cross-section that is selected so as to facilitate movement of the object through a portion thereof;

a piston arranged for movement within the bore with a surface thereof having a contour shaped to cradle the object when the object is propelled out of the bore after being placed therein;

accelerating means for causing the piston to be accelerated so as to cause the object to be cradled on the surface of the piston and propelled out of the bore without touching the sidewalls of the bore; and decelerating means for subsequently causing the piston to be decelerated.

22. The system of claim 17 wherein the measuring means comprises:

a first velocity measuring device for measuring the velocity "v" of the second piece of sports equipment prior to the impact thereof with the center of the predetermined impact area; and a second velocity measuring device for measuring the velocity "V" of the first piece of sports equipment after the first piece of sports equipment has been impacted by the second piece of sports equipment at the center of the predetermined impact area as the first piece of sports equipment rotates about its axis of rotation.

23. A gas cannon for propelling an object placed therein comprising:

a structure having sidewalls which define a bore having a cross-section that is selected so as to facilitate movement of the object through a portion thereof;

a piston arranged for movement within the bore with a surface thereof having a contour shaped to cradle the object when the object is propelled out of the bore after being placed therein;

accelerating means for causing the piston to be accelerated so as to cause the object to be cradled on the surface of the piston and propelled out of the bore without touching the sidewalls of the bore and with substantially no spin thereon; and decelerating means for subsequently causing the piston to be decelerated.

24. The gas cannon of claim 23 wherein the object is a ball.

25. The gas cannon of claim 23 wherein the piston comprises:

first and second pistons being coupled together by a coupling member and being disposed within the bore of the structure for longitudinal movement therein, the second piston having the contour shaped to cradle the object when the object is propelled from the bore; and a baffle comprising an outer surface which fixedly engages the surface of the bore of the structure at a predetermined location to divide the bore into two parts, the baffle defining an aperture through which the coupling member is able to move when the first and second pistons are caused to move by the accelerating/decelerating means.

26. The gas cannon of claim 25 wherein:

the structure defines at least one aperture through one of the sidewalls of the structure, and the bore has a shape selected to house the object therein prior to the object being propelled therefrom; and the decelerating means operates to decelerate the piston when the first piston passes the at least one aperture so as to cause gas trapped between the first piston and the baffle to be compressed and to limit further movement of the piston means.

27. A gas cannon for propelling an object placed therein comprising:

a tube having sidewalls which define a longitudinal bore, and an inlet port at a first end of the tube for selectively receiving a gas into the bore, the size of the bore being selected so as to allow the object to be placed therein;

first and second pistons being coupled together by a coupling member and being disposed within the bore of the tube for longitudinal movement with the first piston being located closer to the inlet port than the second piston, the second piston comprising a major surface for cradling the object such that when the object is propelled from the bore the object does not touch the sides of the bore;

a baffle comprising an outer surface which fixedly engages the surface of the bore of the tube at a predetermined location to divide the bore into two parts, the baffle defining an aperture through which the coupling member is able to move when the first piston is caused to move by the gas entering the inlet port of the tube.

28. The gas cannon of claim 27 wherein the tube has at least one aperture formed through a sidewall thereof, the at least one aperture being located so as to facilitate the escape of any gas in the bore of the tube between the baffle and the first piston while the first piston is located between the inlet port and the at least one aperture, and for facilitating the escape of gas introduced into the inlet port when the first piston is between the at least one aperture and the baffle.

* * * * *